(12) United States Patent
Schneider

(10) Patent No.: US 11,361,852 B2
(45) Date of Patent: *Jun. 14, 2022

(54) COLLECTING APPARATUS AND METHOD

(71) Applicant: David Lyle Schneider, Hong Kong (CN)

(72) Inventor: David Lyle Schneider, Hong Kong (CN)

(73) Assignee: Schneider Advanced Biometric Devices LLC, Sheridan, WY (US)

( * ) Notice: Subject to any disclaimer, the term of this patent is extended or adjusted under 35 U.S.C. 154(b) by 249 days.

This patent is subject to a terminal disclaimer.

(21) Appl. No.: 16/821,990

(22) Filed: Mar. 17, 2020

(65) Prior Publication Data

US 2020/0219598 A1 Jul. 9, 2020

Related U.S. Application Data

(63) Continuation of application No. PCT/US2018/044823, filed on Aug. 1, 2018, which is
(Continued)

(51) Int. Cl.
*H04L 29/06* (2006.01)
*G16H 10/60* (2018.01)
(Continued)

(52) U.S. Cl.
CPC ............ *G16H 10/60* (2018.01); *G06F 21/32* (2013.01); *G06F 21/6245* (2013.01);
(Continued)

(58) Field of Classification Search
CPC ..... G16H 10/60; G06F 21/32; G06F 21/6245; G06F 21/64; H04L 9/06; H04L 9/0866;
(Continued)

(56) References Cited

U.S. PATENT DOCUMENTS 10,468,129 B2   11/2019   Schneider
10,715,724 B2 *  7/2020   Kroepfl .................. G01S 19/49
(Continued)

FOREIGN PATENT DOCUMENTS

CN   HK1244175      3/2018
SE   1750421-8      4/2017
WO   WO2019055147   3/2019

OTHER PUBLICATIONS

PCT International Search Report in PCT/US18/44823, titled "Collecting Apparatus and Collecting Method", Applicant Schneider, David, Lyle, filed Jan. 8, 2018.
(Continued)

*Primary Examiner* — Ghodrat Jamshidi
(74) *Attorney, Agent, or Firm* — Holly Li; Intelink Law Group, P.C.

(57) ABSTRACT

A collecting method records medical transaction declarations by: inputting private information of a patient; requiring two immediate and simultaneous fingerprints, one from each of two persons; displaying prompts for camera photographic images; acquiring the camera photographic images; recording a response through an apparatus display and user-selectable response; prompting for biometric reader activation; recording biometric fingerprints from each of the two persons on each of two physical reader devices, respectively; time-stamping a first fingerprint and a second fingerprint and electronically determining that the two fingerprints are recorded within a time period; computing an electronic decision about the physical proximity of the two persons based upon at least a time-stamp of the first fingerprint and a time-stamp of the second fingerprint; merging biometric signatures from the two persons into an electronic agreement; generating a signed electronic agreement; and output-
(Continued)

ting the signed electronic agreement to permanent storage to memorialize the medical transaction declaration.

19 Claims, 3 Drawing Sheets

Related U.S. Application Data a continuation of application No. 15/707,431, filed on Sep. 18, 2017, now Pat. No. 10,468,129.

(60) Provisional application No. 62/395,514, filed on Sep. 16, 2016.

(51) Int. Cl.
| | | |
|---|---|---|
| *H04L 9/32* | (2006.01) | |
| *H04L 9/06* | (2006.01) | |
| *H04L 9/08* | (2006.01) | |
| *G06F 21/62* | (2013.01) | |
| *G06F 21/64* | (2013.01) | |
| *G06F 21/32* | (2013.01) | |

(52) U.S. Cl.
CPC .............. *G06F 21/64* (2013.01); *H04L 9/06* (2013.01); *H04L 9/0866* (2013.01); *H04L 9/0894* (2013.01); *H04L 9/3231* (2013.01); *H04L 2209/88* (2013.01)

(58) Field of Classification Search
CPC .. H04L 9/0894; H04L 9/3231; H04L 2209/88
See application file for complete search history.

(56) References Cited

U.S. PATENT DOCUMENTS

| | | | | |
|---|---|---|---|---|
| 2004/0199781 | A1* | 10/2004 | Erickson | G16Z 99/00 726/26 |
| 2005/0167484 | A1* | 8/2005 | Sussman | G07C 9/27 235/380 |
| 2011/0199478 | A1* | 8/2011 | Ito | H04N 7/185 348/92 |
| 2013/0002399 | A1* | 1/2013 | Frueh | G07C 9/257 340/5.53 |
| 2013/0251214 | A1* | 9/2013 | Chung | G06K 9/00161 382/116 |
| 2014/0074493 | A1 | 3/2014 | Schneider et al. | |
| 2014/0250450 | A1* | 9/2014 | Yu | H04N 21/4331 725/19 |
| 2015/0223057 | A1* | 8/2015 | Dellarciprete | G16H 10/60 455/410 |
| 2017/0135647 | A1* | 5/2017 | Morris | A61B 5/7275 |
| 2017/0293410 | A1* | 10/2017 | Kulchytskyy | G06F 1/1684 |
| 2018/0121643 | A1* | 5/2018 | Talwerdi | G07C 9/257 |
| 2020/0219598 | A1 | 7/2020 | Schneider | |

OTHER PUBLICATIONS

PCT International Preliminary Report on Patentability in PCT/SE2018/050351, titled "Method Performed By a Computer System for Biometric Authentication of Human Beings of a First or a Second Category," Applicant Safe Patient Identification Sweden AB, filed Apr. 4, 2018.

\* cited by examiner

COLLECTING APPARATUS AND METHOD

CROSS-REFERENCE TO RELATED APPLICATIONS

This application is a continuation of co-pending International Application No. PCT/US18/44823 on COLLECTING APPARATUS AND COLLECTING METHOD as filed on Aug. 1, 2018 in the U.S. Receiving Office of the United States Patent and Trademark Office, which, in turn, claims priority to U.S. application Ser. No. 15/707,431 on BIOMETRIC MEDICAL ANTIFRAUD AND CONSENT SYSTEM as filed on Sep. 18, 2017 in the United States Patent and Trademark Office, the disclosures of which are incorporated by reference herein in their entireties.

TECHNICAL FIELD

The present disclosure generally relates to the protection of personally identifiable data. More particularly, the present disclosure relates to a collecting apparatus and method for reading, encoding and recording biometric data.

DISCUSSION OF RELATED ART

Medical device technology and systems providing healthcare services to the public continue to advance. The public health benefits derived from these technical and informational advancements are significant. Along with the advancements come additional challenges, including privacy and consent issues exacerbated by the complexity and inter-connectedness of medical and health-care industry systems.

An increasing risk has been the proliferation of hacker activity potentially motivated by personal, political, nation-state and/or economic objectives. For the medical industry, this means patients may have heightened concerns about the privacy, accuracy and disclosure of their sensitive health-related information.

Current industry trends tend to address these problems with generic security solutions focused on applications, databases, firewalls and activity alarm systems. One aspect of such approaches, for example, may include proprietary encryption of manufactured storage devices installed in servers and workstations to protect against unauthorized disclosure.

But significant data breaches have occurred, and will likely continue to occur. This has become a serious public problem that may benefit from a combination of multiple enhancements to protect individual privacy. Privacy expectations run high with respect to personally identifiable medical information, in particular.

SUMMARY

An exemplary embodiment collecting apparatus for recording a medical transaction declaration includes: a display unit; an input module configured to receive patient information; a photo collecting module configured to display on the display unit countdown timer instructions for taking photographic images, the photo collecting module including a camera unit configured to take photographic images and store the photographic images in a temporary storage device, and an encoder unit configured to combine and hash the photographic images into a combined data set and store it in the temporary storage device; a fingerprint collecting module configured to display on the display unit instructions for fingerprint capture, fingerprint collecting module including a fingerprint scan unit configured to actuate a fingerprint scan, and a processing unit configured to process the fingerprint scan into a fingerprint template data set and store it in the temporary storage device; a privacy encoder configured to combine and encrypt the data from the temporary storage device into an encrypted data set memorializing the medical transaction declaration; and a purging module configured to purge from the temporary storage device all biometric data acquired by the photo collecting module and the fingerprint collecting module before outputting the encrypted data set.

An exemplary embodiment collecting method for recording a medical transaction declaration includes: inputting private information of a patient; requiring two immediate and simultaneous fingerprints, one from each of two persons; displaying prompts for camera photographic images; acquiring the camera photographic images; recording a response through an apparatus display and user-selectable response; prompting for biometric reader activation; recording biometric fingerprints from each of the two persons on each of two physical reader devices, respectively; time-stamping a first fingerprint and a second fingerprint and electronically determining that the two fingerprints are recorded within a time period; computing an electronic decision about the physical proximity of the two persons based upon at least a time-stamp of the first fingerprint and a time-stamp of the second fingerprint; merging biometric signatures from the two persons into an electronic agreement; generating a signed electronic agreement; and outputting the signed electronic agreement to permanent storage to memorialize the medical transaction declaration.

An exemplary embodiment program storage device, tangibly embodying a program of instruction steps executable by a processor for recording a medical transaction declaration, includes instruction steps for: inputting private information of a patient; requiring two immediate and simultaneous fingerprints, one from each of two persons; displaying prompts for camera photographic images; acquiring the camera photographic images; recording a response through an apparatus display and user-selectable response; prompting for biometric reader activation; recording biometric fingerprints from each of the two persons on each of two physical reader devices, respectively; time-stamping a first fingerprint and a second fingerprint and electronically determining that the two fingerprints are recorded within a time period; computing an electronic decision about the physical proximity of the two persons based upon at least a time-stamp of the first fingerprint and a time-stamp of the second fingerprint; merging biometric signatures from the two persons into an electronic agreement document; generating a signed electronic agreement document; and outputting the signed electronic agreement document to permanent storage to memorialize the medical transaction declaration.

BRIEF DESCRIPTION OF THE DRAWINGS

Aspects of the present disclosure may be appreciated upon consideration of the following description of exemplary embodiments when taken in conjunction with the accompanying drawings, in which.

DETAILED DESCRIPTION

Exemplary embodiments of the present disclosure provide a collecting apparatus and corresponding method for enhancing patient privacy. These and like embodiments may be used with biometric signatures such as fingerprints, face scans, iris scans, or the like, to record patient information into a secure computing system.

Figure 1:
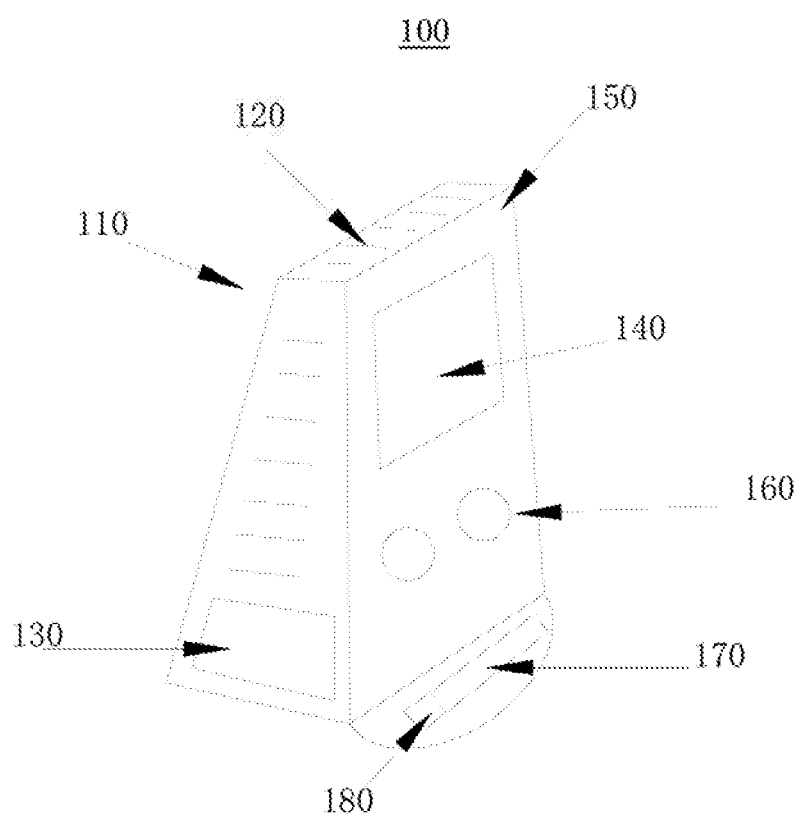
FIG. 1 is a schematic perspective diagram of a collecting apparatus in accordance with an exemplary embodiment of the present disclosure.

As shown in FIG. 1, an exemplary embodiment collecting apparatus is indicated generally by the reference numeral 100. The collecting apparatus 100 includes a casing module 110, an exhaust screen or vents 120, a filtered intake 130 to remove particulate matter and improve reliability of the apparatus in hot and/or dusty field conditions, a display 140 to display instructions for a patient, a metal heat-sink casing 150 to dissipate camera heat or the like, a camera module 160 that may include two or more cameras, where the first camera 162 may be configured to sense normal visible spectrum light and the second camera 164 may be configured to sense thermal, infrared or non-visible spectrum light, for example. The collecting apparatus further includes a fingerprinting portion including, for example, a bar reader 170 configured for multiple-finger scanning and a thumbprint reader 180 configured for thumb or single-finger scanning.

The exemplary embodiment collecting apparatus 100 has a casing module 110 of generally trapezoidal shape in its side view and substantially rectangular shape in its front view, but is not limited thereto. The exhaust screen or vents 120 are preferably formed towards the top and/or side parts of the collecting apparatus, through which heated or exhaust air flows outwards. The intake vent filter 130 is preferably formed towards the bottom part of the collecting apparatus, through which ambient air flows inwards.

The display screen 140 is preferably provided on the front face of the apparatus with a generally rectangular shape. The camera module 160 is provided below the display screen 140, including in the camera module the two different cameras aligned in the horizontal direction, where at least one of the two cameras is for visible light and at least the other camera is for non-visible light, such as infrared or ultraviolet light, but not limited thereto.

The heat-sink casing 150 is made of high thermal conductivity material to dissipate the heat generated by the camera module, for example, and more preferably made of metal. The fingerprint collecting module is preferably provided in the bottom part of the collecting apparatus. The fingerprint collecting module may include at least two fingerprint readers, a first fingerprint reader 170 and a second fingerprint reader 180 that are preferably provided adjacent to each other. Among the two fingerprint readers, one fingerprint reader which has an elongated shape may be configured for multiple-finger scanning, while the other fingerprint reader may be configured for single-finger scanning, such as, for example, thumb scanning.

Inside the casing module, a purging module is configured to purge all temporary data acquired by the photo collecting module and the fingerprint collecting module. The hardware mechanisms within the collecting apparatus of FIG. 1 may be further described with reference to FIG. 2.

Figure 2:
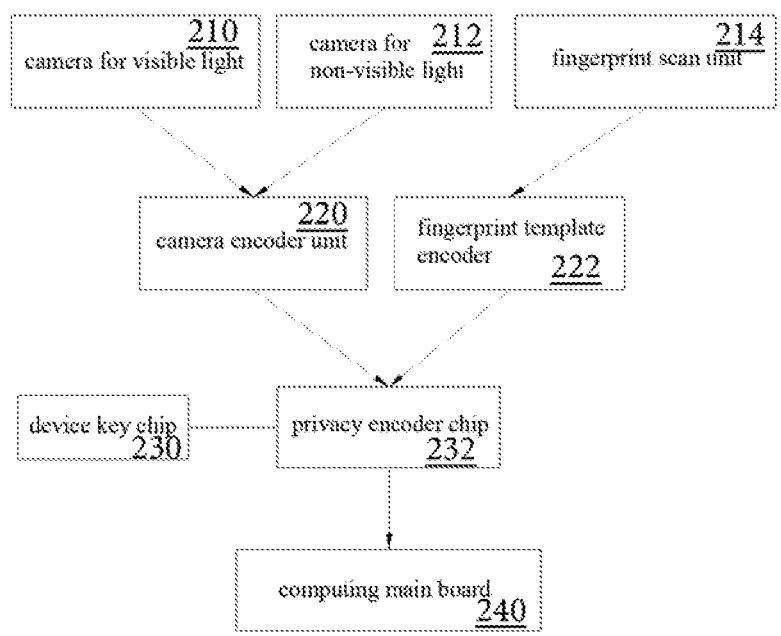
FIG. 2 is schematic hybrid block and signal-flow diagram for a collecting apparatus and method in accordance with an exemplary embodiment of the present disclosure.

Turning to FIG. 2, a collecting apparatus with functional hardware mechanisms and signal flows is indicated generally by the reference numeral 200. The collecting apparatus 200 includes a camera 210 for visible light and a camera 212 for non-visible light, each connected to a camera encoder unit 220. A fingerprint scan unit 214 is connected to a fingerprint template encoder 222. A device key chip 230 as well as both the camera encoder 220 and the fingerprint encoder 222 are each connected to a privacy encoder chip 232, which, in turn, is connected to a computing main board 240.

As shown, the collecting apparatus 200 of FIG. 2 generally indicates exemplary embodiment relationships and an exemplary order of hardware mechanisms in the collecting apparatus 100 of FIG. 1. The process begins at the top of the diagram with acquisition sensors, such as the camera and fingerprint modules, where raw biometric data is received. This unprotected data is encoded by hardware before delivery to temporary storage based on an encryption chip mechanism. The collecting apparatus utilizes a private encryption key which is known only to the apparatus. The hardware encryption mechanism is indicated as a privacy encoder chip, but is not limited thereto.

Figure 3:
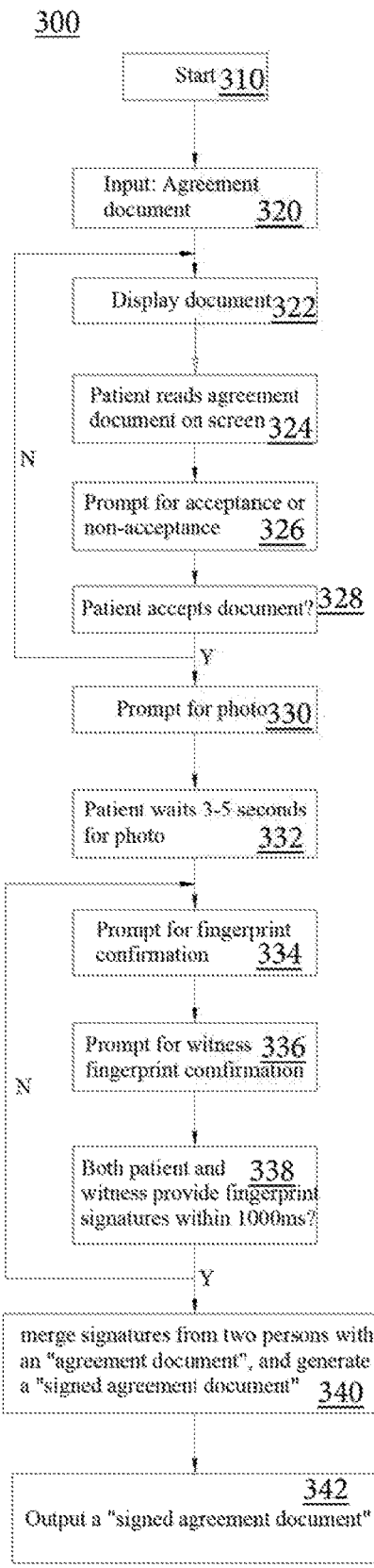
FIG. 3 is a schematic flowchart diagram for a collecting method in accordance with an exemplary embodiment of the present disclosure.

Turning now to FIG. 3, a collecting method is indicated generally by the reference numeral 300. The method includes a start block 310 that passes control to an input/output block 320. The block 320 receives an input agreement document, and passes control to an input/output block 322. The block 322 displays the document, and passes control to a function block 324. The function block 324 enables the patient to read the agreement document, such as on a screen, and passes control to an input/output block 326. The block 326 prompts the patient for acceptance or non-acceptance of the agreement, and passes control to a decision block 328. If the patient does not accept the agreement, the decision block 328 passes control back to block 322. If the patient does accept the agreement, the decision block 328 passes control on to an input/output block 330.

The input/output block 330, in turn, prompts the patient to be photographed, and passes control to a function block 332. The block 332 enables a photograph to be taken of the patient, such as within three to five seconds, and passes control to an input/output block 334. The block 334 prompts for patient fingerprint confirmation, and passes control to an input/output block 336. The block 336 prompts for witness fingerprint confirmation, and passes control to a decision block 338. If the patient and the witness do not both provide fingerprint confirmations within a predetermined period of time, such as 1000 ms, the decision block passes control back to block 334. If the patient and the witness do both provide fingerprint confirmations within the predetermined period of time, the decision block passes control on to function block 340.

The block 340, in turn, merges the signatures from the patient and the witness into the agreement document, generates a signed agreement document, and passes control to an input/output block 342. The block 342 outputs a signed agreement document, and passes control to an end block.

In operation of exemplary embodiments with respect to FIGS. 1, 2 and 3, preferred embodiments may record transactions in real-time such as may be required for auditing purposes. An exemplary embodiment of the present disclosure relates to a collecting apparatus, such as segregated custom-purpose hardware but not limited thereto, that reads, encodes and records patient biometric data, and purges all raw and intermediate biometric data once finalized or encrypted data has been provided for secure storage.

The exemplary collecting apparatus includes an input module configured to input patient information; a photo-collecting module connected to a display unit configured to display countdown timer instructions for taking photographic images, and includes a camera unit configured to take photographic images and store the photographic images in a temporary storage device, such as one that can scramble and encode private information but not limited thereto, and an encoder unit that combines and hashes the photographic images into a combined data set and forwards the combined data set, such as encoded photographic images but not limited thereto, to a privacy encoded temporary storage; a fingerprint collecting module including a display unit configured to display instructions for fingerprint capture, a fingerprint scan unit configured to actuate fingerprint scan, and a processing unit that processes fingerprint scans into a fingerprint template data set; a privacy encoder unit configured to combine and encrypt all data acquired into an encrypted data set; a purging module configured to purge all temporary data acquired by the photo collecting module and the fingerprint collecting module; and a casing module in which the photo collecting module, the fingerprint collecting module, and the purging module are arranged, including filter vents, an exhaust vent screen, and an intake vent filter configured to remove particulate matter and improve reliability of the apparatus.

The exemplary collecting apparatus may delete original biometric data upon delivery to a computing main board and/or software. The collecting apparatus may deliver resulting biometric data in an encoded and encrypted data set to the computing main board for permanent storage.

The exemplary collecting apparatus may scramble and encode private information in a manner that cannot be reasonably deciphered outside of the apparatus. This may allow for permanent storage of such biometric information, such as scrambled without external cipher keys but not limited thereto, with reduced risk of compromise by code viruses, theft and/or loss of system data from cloud, private network, or insurance industry data warehouse systems, for example.

While exemplary embodiments are chosen for descriptive purposes, it shall be understood by those of ordinary skill in the pertinent art that such and like embodiments may be adapted to complex systematic and biometric workflow systems, for example. Moreover, there are numerous possibilities and variations in the medical, finance and other marketplaces to which embodiments of the present disclosure may be directly applied or reasonably adapted.

For example, the camera unit or module may include two cameras. One of the two cameras may be for visible light and the other for non-visible light, and the two cameras may be aligned to take a photo in the same direction. Further, the fingerprint scan unit may include two fingerprint readers, one of the two fingerprint readers being for one finger such as a thumbprint reader, and the other being for multiple fingers such as a fingerprint bar reader, and the two fingerprint readers may be located proximate to each other.

An exemplary embodiment collecting method for recording a medical transaction declaration includes the steps of inputting private information of a patient; requiring two immediate and simultaneous fingerprints; displaying prompts for camera photographic images; acquiring camera photographic images; recording an affirmative or negative response through an apparatus display; receiving a user-selectable response; prompting for a biometric reader activation; recording biometric fingerprints from two persons on two physical reader devices; time-stamping a first fingerprint and a second fingerprint and electronically determining that the two fingerprint s are recorded within a certain time period; computing an electronic decision about the physical proximity of the two persons based upon a time-stamp of the first fingerprint and a time-stamp of the second fingerprint; merging biometric signatures from the two persons with an "agreement document", generating a "signed agreement document"; and outputting a "signed agreement document" to a computing main board.

The exemplary collecting method may be applied to private information including name of patient, identifying number of patient, and/or date of birth of patient, where the response includes an affirmative response or a negative response. The collecting method may be applied where the certain time period is 10 seconds, for example. The collecting method may be applied where the two persons include a patient and a witness, for example.

Using the exemplary collecting apparatus and exemplary method together as described herein, patient privacy may be protected while recording highly private personal data about each individual. This is a challenging application, particularly considering that high-level government and insurance industry regulations already require, in a systematic way, collection of biometric information such as fingerprints, photographic images, and other data based upon personal characteristics of individuals.

Exemplary embodiments may be implemented in dedicated hardware and/or software without limitation. For example, while a highly-specific, specialized apparatus is provided to protect patient privacy while recording private and personal data about an individual, at least some of the functionality may optionally be embodied in software. Such solutions are adaptable based on specific requirements, such as, for example, government and/or industry regulations or goals, where collecting biometric information is either an end-goal or but a small step in a larger process. For example, positive identification readers may improve safety and facilitate audits of potential financial fraud abuses in complex high-value industries.

Embodiments of the present disclosure may incorporate existing fingerprint reader devices, biometric lock devices, access-authorization-auditing electronic system access controls, and healthcare data processing systems and databases. For example, embodiments may be adapted for computing devices with integrated fingerprint readers, fingerprint reader hardware in law enforcement and customs identification applications, biometric door locks, systematic face scanning and/or facial recognition, financial industry transaction systems, security agency hardware encryption, or the like.

An exemplary embodiment collecting apparatus may be disposed in a sealed enclosure, such as for intermittent use and/or with an external heat-sink. The collecting apparatus may include a casing module, a display screen which displays written instructions provided to the patient, a metal heat-sink casing for dissipating camera heat, one or two camera modules for acquiring images based on normal visible light as well as thermal, infrared or non-visible-light, a fingerprint bar reader for multiple-finger scanning; and a thumbprint reader for thumb or single-finger scanning. The collecting apparatus may have a trapezoidal shape in its side view and a substantially rectangular shape in its front view, or may be shaped differently to increase surface area for heat dissipation. The display screen is preferably provided hi the front face of the apparatus and may have a rectangular shape. A camera module is provided below the display screen, including in the camera module two different cameras aligned in the height or vertical direction, where one of the two cameras is for visible light and the other is for non-visible light. The casing is made of material that readily dissipates heat generated by the camera module, and is preferably made of metal.

The exemplary fingerprint collecting module is preferably provided in the bottom part of the collecting apparatus, preferably including at least one of the two fingerprint readers, which are preferably provided adjacent to each other. Among the two fingerprint readers, one fingerprint reader which may have a more elongated shape may be used for multiple-finger scanning, while the other fingerprint reader may be used for single-finger scanning, such as, for example, thumb scanning. A sensor data purging module is provided inside the casing module, and configured to purge all temporary data acquired by the photo collecting module and the fingerprint collecting module.

The exemplary collecting apparatus includes acquisition hardware and other hardware mechanisms such as at least one encoding and/or recoding device, which operate in unison where raw biometric data is input. This unprotected data is encoded by hardware before delivery to temporary storage based on an encryption chip mechanism. The collecting apparatus utilizes a private encryption key which is known only to the device. The hardware encryption apparatus, and the hardware encryption mechanism, may comprise a uniquely coded privacy encoder chip.

The exemplary collecting method demonstrates how a private biometric signature may be used to confirm a real-time medical transaction. For the prevention of medical fraud, the method steps demonstrate how a patient may review a document and then certify with a witness, using a dedicated real-time apparatus with hardware encryption in this example.

An agreement document is input and/or displayed. Then, the collecting apparatus that reads, records and encodes, prompts for acceptance or non-acceptance. If the patient matching the biometric data acknowledges and accepts the document, a corresponding medical identification number is generated or input, and each of the patient's surname, given name, and date of birth are input or confirmed. Next, the apparatus displays a countdown timer with optional instructions for a photograph, and at least one camera mechanism acquires a photographic image, which it saves to temporary storage. Similarly, the non-visible-light camera mechanism acquires an image and saves that in temporary storage as well. The photographic encoder chip combines and/or hashes the two photographic images into a combined data set, and forwards the combined data set, including the encoded private photographic images, to a privacy encoder temporary storage area.

The exemplary apparatus also displays instructions for fingerprint capture, and actuates at least one fingerprint scan. It processes the fingerprint scan into a fingerprint template data set; and a fingerprint encoder chip forwards a combined data set including unencrypted fingerprint template data to the privacy encoder temporary storage. The privacy encoder communicates with a device key chip delivering an encryption key unique to session recording, and then combines and independently encrypts all data acquired including agreement, patient name, date of birth, patient responses, encoded photographic image data, and encoded fingerprint template data into an encrypted data set. The apparatus purges all temporary data including unencrypted photographic images, fingerprint scans, and fingerprint templates such that the combined mechanisms delete original biometric data within the apparatus upon delivery to a computing main board and/or software. Thus, the apparatus delivers the resulting biometric data in an encoded and/or encrypted data set to a computing main board for permanent storage.

An exemplary hardware encryption device is preferably embodied in a compact, durable form including a camera module having a first camera for acquiring visible-light images and a second camera for acquiring non-visible-light images, such as infrared and/or ultraviolet, where the two cameras align to acquire images from substantially the same direction. The device includes a fingerprint module including a first fingerprint reader preferably for one finger, and a second fingerprint reader preferably for multiple fingers, where the second fingerprint reader is preferably located proximate to the first fingerprint reader. A privacy module includes a first chip that converts acquired photographic images into an encoded photo data set, and a second chip that converts acquired fingerprints into an encoded fingerprint data set template. A device key chip is connected to the privacy module for providing a unique encoded symmetric device key. A hardware encryption processor is connected to the privacy module. All modules are physically separated with hardware connection boundaries that precludes malicious virus software, or the like, such that only the hardware encryption processor is connected to any computing main board.

The exemplary recording method is embodied within a compact device for completing a medical transaction declaration record, such that a real-time transaction encodes in a manner preventing forgery or tampering. The method includes activating at least two fingerprint readers that, when activated, requires two immediate and substantially simultaneous fingerprints. The device display prompts for camera photographic images, and then acquires photographic images with the cameras. The device includes a hardware encryption module for encoding and encrypting of the recorded record data.

When the exemplary apparatus prompts for photographic images, the patient preferably waits 3-5 seconds for the photographic images to be acquired; and, if the patient does not accept the document, the process returns back to the first step. After taking the photographic images successfully, the process goes on to the next step, where biometric fingerprints are required to confirm the identities of the patient and the witness. The fingerprint s from these two persons are preferably recorded on two physical reader devices. Next, the collecting apparatus time-stamps each biometric fingerprint and electronically determines that the fingerprints were recorded within a certain time period, such as, for example, about one to 10 seconds.

The exemplary device computes an "agreement document", such as using Portable Document Format (PDF), and stores it in device memory. It displays the "agreement document" on the device display. The device records an affirmative or negative response through the device display and at least one user-selectable response. It prompts for biometric reader activation, and records biometric fingerprints from two persons, preferably on two physical reader devices. The device time-stamps each biometric fingerprint and electronically determines that that fingerprints were both recorded within about 1000 ms (1 second) of each other.

An exemplary apparatus makes an electronic decision about the physical proximity of the two people, such as one patient and one witness, based upon the first fingerprint reader time-stamp and the second fingerprint reader time-stamp. If it determines that the fingerprints were recorded within a predetermined period, such as 10 seconds, the apparatus merges the biometric signatures from the two persons with an "agreement document", thereby generating a "signed agreement document". But if it determines that the fingerprints were not recorded within 10 seconds of each other, the process returns to the fingerprint scan step. Then the "signed agreement document" is output to a computing main board, and the process is complete.

An exemplary specialized apparatus is thereby provided for recording medical transactions designed to protect patient privacy and record private biometric individually identifiable data. The mechanisms and proprietary methods may scramble, hash, encode and/or encrypt the biometric data within the recording device, rendering it unrecoverable with high assurance upon leaving the recording device, while a secure audit copy is provided for permanent storage and/or external systems.

Heretofore, the present disclosure has been described with reference to exemplary embodiments, but the invention is not limited thereto. The disclosed and alternate embodiments of the present disclosure may be subjected to various modifications and improvements by those of ordinary skill in the pertinent art without departing from the scope or spirit of the present disclosure at set forth in the appended claims or their equivalents.

What is claimed is:

1. A collecting apparatus for recording a medical transaction declaration, comprising:
   a plurality of processors;
   a display unit;
   an input module configured to receive one or more persons information;
   a photo collecting module configured to display on the display unit countdown timer instructions for taking photographic images of the one or more persons, the photo collecting module including a camera unit configured to take photographic images and store the photographic images of the one or more persons in a temporary storage device, and an encoder unit configured to combine and hash the photographic images of the one or more persons into a combined data sets and store the combined data sets in the temporary storage device;
   a fingerprint collecting module configured to display on the display unit instructions for fingerprint capture of the one or more persons, the fingerprint collecting module including a fingerprint scan unit configured to actuate a fingerprint scan of the one or more persons, and a processing unit configured to process the fingerprint scan of the one or more persons into fingerprint template data sets and store the fingerprint template data sets in the temporary storage device;
   a privacy encoder configured to combine and encrypt the combined data sets and fingerprint template data sets from the temporary storage device into encrypted data sets memorializing the medical transaction declaration; and
   a purging module configured to purge from the temporary storage device all biometric data acquired by the photo collecting module and the fingerprint collecting module before outputting the encrypted data sets.

2. The collecting apparatus of claim 1, further comprising a casing module in which the photo collecting module, the fingerprint collecting module, and the purging module are arranged, including filter vents, an exhaust vent screen, and an intake vent filter configured to remove particulate matter.

3. The collecting apparatus of claim 1, wherein the fingerprint scan unit includes a plurality of fingerprint readers, at least a first of the plurality of fingerprint readers is for one finger and at least a second of the plurality of fingerprint readers is for multiple fingers.

4. The collecting apparatus of claim 3, wherein at least the first and at least the second of the plurality of fingerprint readers are located in positions wherein two or more immediate or substantially simultaneous fingerprints can be generated from the plurality of fingerprint readers.

5. The collecting apparatus of claim 1, wherein the camera unit includes a plurality of cameras aligned to acquire photographic images in a substantially same direction, at least a first of the plurality of cameras configured to image visible light and at least a second of the plurality of cameras configured to image invisible radiation.

6. The collecting apparatus of claim 5, wherein the invisible radiation is at least one of ultraviolet spectrum radiation, near-infrared spectrum radiation, or far-infrared spectrum radiation.

7. The collecting apparatus of claim 1, wherein the photo collecting module includes a plurality of camera units or a facial recognition unit.

8. The collecting apparatus of claim 7, wherein each of the plurality of camera units includes a respective plurality of cameras aligned to acquire photographic images in a substantially same direction per unit, at least a first of each respective plurality of cameras configured to image visible light and at least a second of each respective plurality of cameras configured to image invisible radiation.

9. A collecting method for recording a medical transaction declaration, comprising:
   inputting private information of a patient;
   requiring two immediate and simultaneous fingerprints, one from each of two persons;
   displaying prompts for camera photographic images;
   acquiring the camera photographic images;
   recording a response through an apparatus display and user-selectable response;
   prompting for biometric reader activation;
   recording biometric fingerprints from each of the two persons on each of two physical reader devices, respectively;
   time-stamping a first fingerprint and a second fingerprint and electronically determining that the two fingerprints are recorded within a time period that is no more than 10,000 milleseconds;
   computing an electronic decision about the physical proximity of the two persons based upon at least a time-stamp of the first fingerprint and a time-stamp of the second fingerprint;
   merging biometric signatures from the two persons into an electronic agreement;
   generating a signed electronic agreement; and
   outputting the signed electronic agreement to permanent storage to memorialize the medical transaction declaration.

10. The collecting method of claim 9, wherein the private information includes last name, first name, and middle initial of the patient, identifying medical number of the patient, and date of birth of the patient; and the response includes an affirmative response and a negative response.

11. The collecting method of claim 9, further comprising performing facial recognition on at least one of the acquired photographic images, wherein the two persons include the patient and a witness.

12. The collecting method of claim 9, wherein:
   at least a first of the acquired camera photographic images represents detected humanly-visible light, and at least a second of the acquired camera photographic images represents detected near-infrared spectrum electromagnetic radiation.

13. The collecting method of claim 9, wherein:

at least a first of the acquired camera photographic images represents detected humanly-visible light, and at least a second of the acquired camera photographic images represents detected far-infrared thermal spectrum electromagnetic radiation.

14. A non-transitory program storage embodying a program of instruction steps executable by a processor for recording a medical transaction declaration, the instruction steps comprising:

inputting private information of a patient;

requiring two immediate and simultaneous fingerprints, one from each of two persons;

displaying prompts for camera photographic images;

acquiring the camera photographic images;

recording a response through an apparatus display and user-selectable response;

prompting for biometric reader activation;

recording biometric fingerprints from each of the two persons on each of two physical reader devices, respectively;

time-stamping a first fingerprint and a second fingerprint and electronically determining that the two fingerprints are recorded within a time period that is no more than 10,000 milleseconds;

computing an electronic decision about the physical proximity of the two persons based upon at least a time-stamp of the first fingerprint and a time-stamp of the second fingerprint;

merging biometric signatures from the two persons into an electronic agreement document;

generating a signed electronic agreement document; and outputting the signed electronic agreement document to permanent storage to memorialize the medical transaction declaration.

15. The program storage device of claim 14, wherein the private information includes last name, first name, and middle initial of the patient, identifying medical number of the patient, and date of birth of the patient; and the response includes an affirmative response and a negative response.

16. The program storage device of claim 14, further comprising performing facial recognition on at least one of the acquired photographic images, wherein the time required is no more than 10,000 milliseconds.

17. The program storage device of claim 14, wherein the two persons include the patient and a witness.

18. The program storage device of claim 14, wherein:

at least a first of the acquired camera photographic images represents detected humanly-visible light, and at least a second of the acquired camera photographic images represents detected near-infrared spectrum electromagnetic radiation.

19. The program storage device of claim 14, wherein:

at least a first of the acquired camera photographic images represents detected humanly-visible light, and at least a second of the acquired camera photographic images represents detected far-infrared thermal spectrum electromagnetic radiation.

* * * * *